United States Patent [19]
Boutelle

[11] Patent Number: 5,963,335
[45] Date of Patent: Oct. 5, 1999

[54] MEANS AND METHOD FOR MEASURING ABSORPTION OF RADIATION-SCATTERING SAMPLES

[75] Inventor: Steven J. Boutelle, Rogers, Minn.

[73] Assignee: Waters Instruments, Inc., Rochester, Minn.

[21] Appl. No.: 09/103,782

[22] Filed: Jun. 24, 1998

Related U.S. Application Data

[60] Provisional application No. 60/050,696, Jun. 25, 1997.
[51] Int. Cl.$^6$ ...................................................... G01N 21/00
[52] U.S. Cl. .............................. 356/433; 356/436; 356/39
[58] Field of Search ..................................... 356/432, 433, 356/434, 435, 436, 440, 39, 437, 73, 236; 250/339.13, 565, 228

[56] References Cited

U.S. PATENT DOCUMENTS

| | | | |
|---|---|---|---|
| 3,694,086 | 9/1972 | May | 356/307 |
| 3,724,952 | 4/1973 | Vossberg | 356/432 |
| 4,101,221 | 7/1978 | Schunck et al. | 356/434 |
| 4,892,409 | 1/1990 | Smith | 356/440 |

*Primary Examiner*—Hoa Q. Pham
*Attorney, Agent, or Firm*—Fredrikson & Byron, PA

[57] ABSTRACT

The present invention provides methods and devices for measuring radiation absorption by a sample. The invention enables one to determine whether the sample scatters the radiation of interest and, if so, to factor out the effects of such scattering and ore accurately determine the true absorption of the sample. The invention may employ a selectively controllable occluder which is moved between three or more different positions to yield three or more different radiation measurements. These measurements can then be compared to one another to determine the nature of any radiation scattering and factor out its effects, enabling more accurate absorption determinations.

31 Claims, 7 Drawing Sheets

MEANS AND METHOD FOR MEASURING ABSORPTION OF RADIATION-SCATTERING SAMPLES

This application claims priority to U.S. Provisional Application No. 60/050,696 filed Jun. 25, 1997.

FIELD OF THE INVENTION

The present invention provides a device for effectively measuring the absorption of a radiation spectrum for a sample which also scatters the radiation. The invention has particular utility in measuring the absorption of light in whole blood and other biologic samples as a means for conducting chemical analysis of the sample.

BACKGROUND OF THE INVENTION

A wide variety of analytical chemical techniques measure a sample's absorption of radiation at a particular wavelength or series of wavelengths. Often times, the absorption of this specified radiation will vary in a predefined relationship with respect to some specific chemical or physical property of the sample, such as density or concentration. Accordingly, by measuring the absorption of a sample at the specified wavelength or wavelengths, one can frequently determine the density or concentration of some component of the sample.

For example, when radiant energy passes through a liquid, certain wavelengths of that energy may be selectively absorbed by particles which are dissolved in that liquid. For a given path length which the light traverses through the liquid, Beer's law (also referred to as the Beer-Lambert relationship) indicates that the relative transmittance of the liquid at a given wavelength is inversely logarithmically related to the concentration of the solute which absorbs that wavelength. Accordingly, for a sample having a predetermined path length, the transmittance of a sample at the specified wavelength should permit one to fairly readily determine the concentration of the solute which absorbs at that wavelength.

This principle is commonly used in hemoglobinometers, which are essentially specialized spectrophotometers used to measure the concentration of hemoglobin in a sample. By directing a light at a specified wavelength or series of wavelengths into a sample of a known thickness and measuring the intensity of the light passing through the sample, one can effectively determine the concentration of one or more species of hemoglobin in the sample. Such a process is discussed in U.S. Pat. No. 4,357,105 (Loretz) and in U.S. Pat. No. 3,994,585 (Frey), the teachings of both of which are incorporated herein by reference.

The utilization of transmittance as a measure of concentration can provide fairly accurate results in a simple, efficient manner. Unfortunately, this measurement is subject to a number of variables. Some of these variables are dependent on the measuring device itself, such as the nature of the light being emitted by the light source, the spectral response of the other optical components interposed between the light source and the detector, temperature within the system, etc. By utilizing appropriate controls and frequent calibration, such variables can be effectively determined and factored out of any transmittance measurements.

There are some variables which are sample-dependent, though. One such variable which can present significant difficulties in measuring the light attenuation due to absorption of the sample is the presence of scattering particles. If a sample is non-scattering, the total transmittance measured for the sample can provide an accurate measurement of the absorption attributable to the presence of the solute of interest. However, if the sample also scatters the wavelength of radiation of interest, this scattering can significantly impact the measured transmittance of the sample and yield inaccurate analytical results.

The losses attributable to scattering have two primary components. The first is the radiation scattered away from the detector which will never reach the detector at all. The other component is related to the fact that the scattering particles will significantly increase the mean path length of radiation passing through the sample as the radiation bounces from one scattering particle to another on the way to the detector. Since Beer's law is based on an assumption that the path length through the fluid will remain constant, such an increase in the mean path length can have a marked impact on the calculated concentration of the solute.

FIG. 10 illustrates the impact of scattering in a blood sample. Whole blood is made up primarily of plasma and red blood cells, which tend to scatter light. (White blood cells and platelets play a minor role due to the quantity involved.) The presence of the red blood cells, therefore, can have a significant impact on the measured optical density (i.e., the negative of the logarithm of the transmittance value). For this reason, many of the more accurate blood analyzers mechanically or chemically lyse the sample, i.e. break down the cell walls of the red blood cells, before taking any measurements. Since it is the change in the index of refraction of the sample at the surface of the red blood cells that causes scattering, lysing will allow one to achieve a virtually non-scattering sample.

Unfortunately, lysing a sample adds its own complexities. Of one mechanically lyses the sample, this is commonly done in a length of flexible tubing through which each sample must pass. This significantly increases the risk of cross-contamination between the samples. If one chemically lyses the sample, this will dilute the original sample and can make it more difficult to detect smaller hemoglobin concentrations. On addition, lysing will not remove all scattering particles. Sometimes blood includes a not insignificant amount of other light-scattering particles, such as fat particles, and certain drugs, such as one sold under the trade name Interlipid, can also affect scattering. In addition, if lysis is incomplete, the non-lysed cells will continue to scatter light.

FIG. 10 schematically illustrates the relationship between the optical density of a sample and the total hemoglobin concentration [THb]. There are two curves depicted in FIG. 10. The lower curve, shown in dashed lines, is the optical density for a lysed blood sample. The slope of this line is constant since the only impact on optical density is the hemoglobin concentration. It should be noted that this graph is somewhat idealized in that a variety of other factors could impact the optical density, as noted above, but those factors are ignored in FIG. 10.

The upper curve, shown in solid lines, is the optical density for a whole blood sample. The slope of this line varies depending on the hemoglobin concentration. Hemoglobin is retained within red blood cells. Generally speaking, therefore, the higher the total hemoglobin in the blood sample, the higher the number of light-scattering red blood cells there will be. As noted above, light-scattering particles will significantly reduce the transmittance, increasing the measured optical density. For this reason, the scattering curve is positioned above the lysed curve along most of its length in FIG. 10. The difference in the measured optical density at any given concentration is indicated as an offset S.

The value of this offset S will differ depending on the concentration of the red blood cells in the sample. Between two end points, indicated as A and B, in FIG. 10, this scattering offset S will remain substantially constant and the slope of the two curves will remain substantially identical. On either end of this range, though, this offset will vary.

In any scattering sample, the offset S will depend on the relative indices of refraction of the scattering particles and the medium in which they are suspended. In the case of whole blood, the plasma, red blood cell walls and the liquid within those cell walls each have different refractive indices. This causes light to bend as it passes from plasma, through the cell wall to the intracellular fluid, and back out again. In addition, since the different refractive indices of the various materials means that the light passes through those materials at different rates, these differences in the indices of refraction will affect the effective light path length through the sample.

Coherent light sources produce light rays with a fixed phase relationship with one another. When the light rays are in phase with one another, their wave maxima will constructively combine to produce a higher total light intensity. If a sample is non-scattering, the path length through the sample is the same for each ray of light, so the phase relationship between the rays remains the same when light passes through the sample. As a result, the rays exiting the sample remain coherent and the wave maxima of the light rays constructively combine.

If the sample is scattering, the path length for each ray is different due to differences in the media through which the light must pass to traverse the sample. As a result, the original phase relationship of the light rays is lost and at least some of the light rays may destructively combine. As the particle concentration of the sample increases, the phase relationship between the light rays is increasingly lost until the phase relationship between any two rays of light exiting the sample is essentially completely random. At this point, the light exiting the sample is said to be "incoherent" and the sample is said to be incoherently scattering.

As the sample becomes increasingly scattering, the light goes from being completely coherent (as in the case of Hct=0 in FIG. 10) to progressively increasing incoherence. As a result, the offset S in FIG. 10 progressively increases from an initial value of zero as the THb value (which is related to the number of light scattering red blood cells, as noted above) increases. Once the light exiting the sample becomes incoherent, though, the offset attributable to such losses will remain fairly constant.

The scattering which occurs at lower particle densities is referred to as "coherent" scattering. "Incoherent" scattering, which occurs at higher particle densities, produces a substantially constant scattering loss over a fairly wide range of particle concentrations due to the essentially random nature of the interaction with the particles. At even higher particle concentrations, the sample begins to scatter coherently again. In essence, the sample can be viewed as scattering particles with a liquid interspersed between those particles, which induces behavior similar to a liquid with particles dispersed throughout the liquid.

Generally, one would expect the sample to be essentially completely incoherently scattering at a hematocrit fraction (Hct) of about 0.25 at the lower end, which will generally correspond to a point where A in FIG. 10 is about 8 g/dL. In a healthy individual, the hemoglobin concentration of the blood will tend to be about 16 g/dL for male adults and about 15 g/dL for female adults. Accordingly, most samples will fall within the incoherent scattering range and have a fixed, predictable increase in optical density attributable to scattering, shown in FIG. 10 as the offset S. However, it is not particularly unusual to have patient samples with hemoglobin concentrations significantly above or below this norm. Some of those samples will fall in the coherent scattering region, which will have a lower, less readily predictable offset S.

Many whole blood hemoglobinometers described in the literature do not take into account the possibility that a patient's hemoglobin concentrations could fall within the coherently scattering ranges. Instead, a fixed offset S is subtracted from every optical density measurement before calculating the hemoglobin concentration. Obviously, the more one deviates from incoherent scattering (e.g., the lower the concentration below the level A in FIG. 10), the more inaccurate the calculated hemoglobin concentration will be. Unfortunately, with current mechanisms, there is no way to determine the transmission losses attributable to scattering on a sample-by-sample basis. Accordingly, if a physician needs to accurately determine lower hemoglobin concentrations, the patient's sample must be analyzed in a different analyzer which will lyse the sample.

SUMMARY OF THE INVENTION

The present invention provides a method and a device for measuring the absorption of radiation by a sample which can take into account the scattering effects of particles in the sample. In accordance with a first method of the invention, an analyzer is provided which includes a radiation source, a sample holder, a radiation detector, and a selectively operable radiation occluder positioned between the source and the detector along a radiation path. A sample is placed in the sample holder and the occluder is positioned at a first position. While the occluder is in that first position, radiation is directed from the source toward the sample and a first radiation measurement is taken with the detector.

Next, the occluder is positioned at a second position wherein the percentage of radiation occluded by the occluder is different from the percentage of radiation occluded in the first position. The radiation is directed from the source toward the sample and a second radiation measurement is taken with the detector. The occluder is positioned at a third position, with the percentage of radiation occluded by the occluder in the third position being different from the percentage of radiation occluded in either of the first or second positions. Radiation is once again directed from the source toward the sample and a third radiation measurement is taken with the detector.

The first, second and third radiation measurements are then compared to determine the radiation attenuation attributable to scattering by the sample. This radiation attenuation attributable to scattering can then be factored out to determine a radiation absorption value of the sample.

A second method in accordance with the invention is somewhat more specific to measuring light absorption by a light-scattering sample. In accordance with this method, an analyzer is provided which includes a light source, a sample holder, a light detector and a selectively operable occluder positioned between the source and the detector along a light path. Once again, a sample is placed in the sample holder and the occluder is positioned at the first position. Light is directed from the source toward the sample and a first light measurement is taken with the detector. As in the previous embodiment, a second light measurement is taken with the detector with the occluder at a second position wherein the percentage of light occluded by the occluder and the second position is different from that occluded in the first position. A third light measurement is taken with the occluder in a third position wherein the percentage of light occluded by the occluder is different from that in either of the first or second positions. The first, second and third light measurements are then compared to determine light attenuation attributable to scattering caused by the sample and this scattering attenuation is then factored out to determine a light absorption value for the sample.

The present invention also contemplates an analyzer which can be used to measure light attenuation of a sample attributable to absorption when the sample may have scattering particles therein. This analyzer includes a light source, a sample container, a light detector, a selectively controlled light occluder and a motor. The light occluder is positioned between the light source and the light detector along a light path. The occluder may include a plate having an area which is highly transmissive of light at a predetermined wavelength and at least one area which is less transmissive at that wavelength. The motor is adapted to move the occluder between a first position wherein the plate is positioned relative to the light path to occlude a first percentage of the light, a second position wherein the plate is positioned relative to the light path to occlude a second percentage of the light, and a third position wherein the plate is positioned relative to the light path to occlude a third percentage of the light. By appropriately controlling the motor and the light source and/or detector, one can effectively carry out one of the methods mentioned above.

DETAILED DESCRIPTION OF THE PREFERRED EMBODIMENTS

Figure 1:
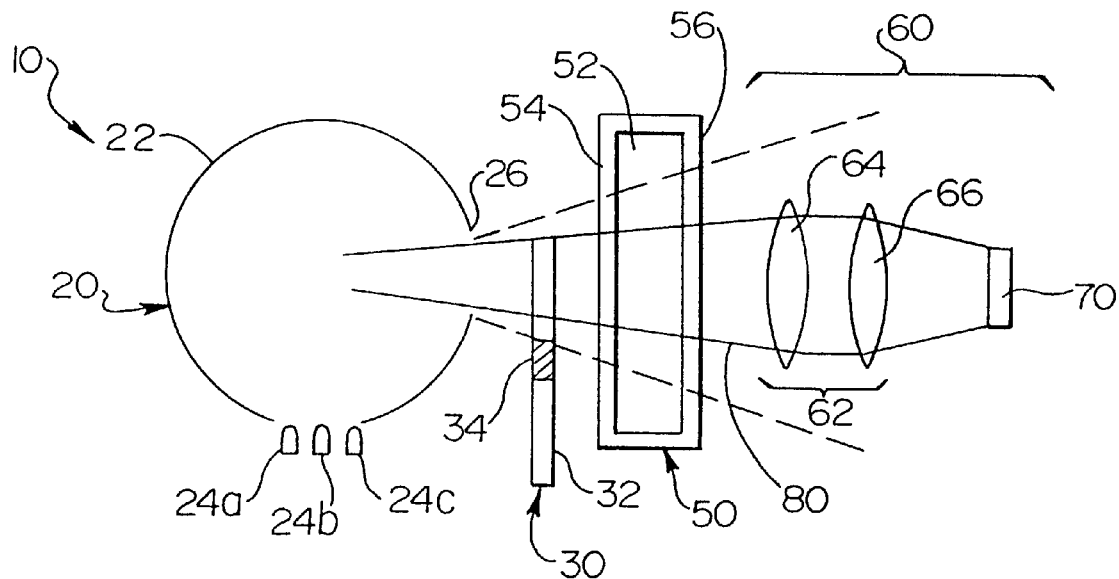
FIG. 1 is a schematic illustration of an analyzer in accordance with the invention with an occluder in a first position.
Figure 2:
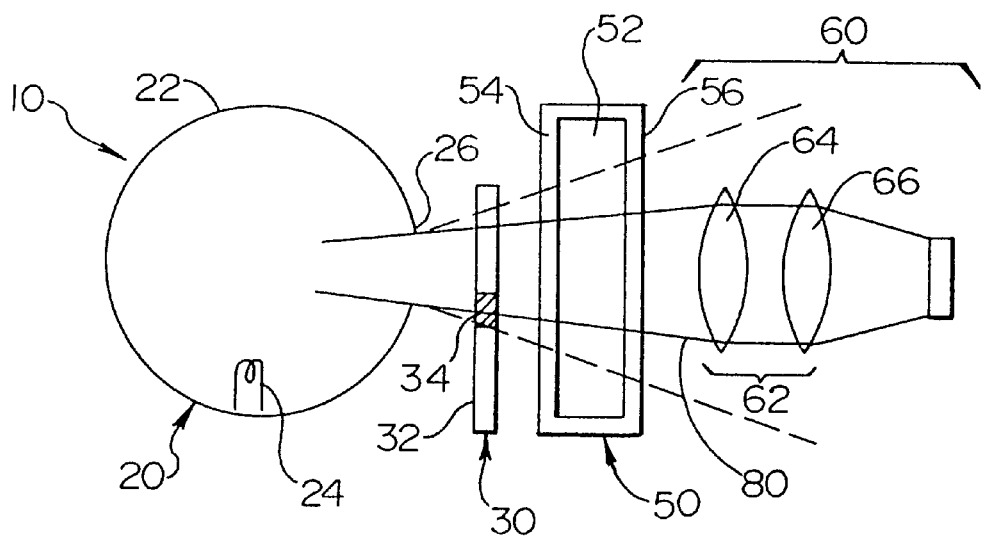
FIG. 2 is a schematic illustration of the analyzer of FIG. 1 with the occluder in a second position.
Figure 3:
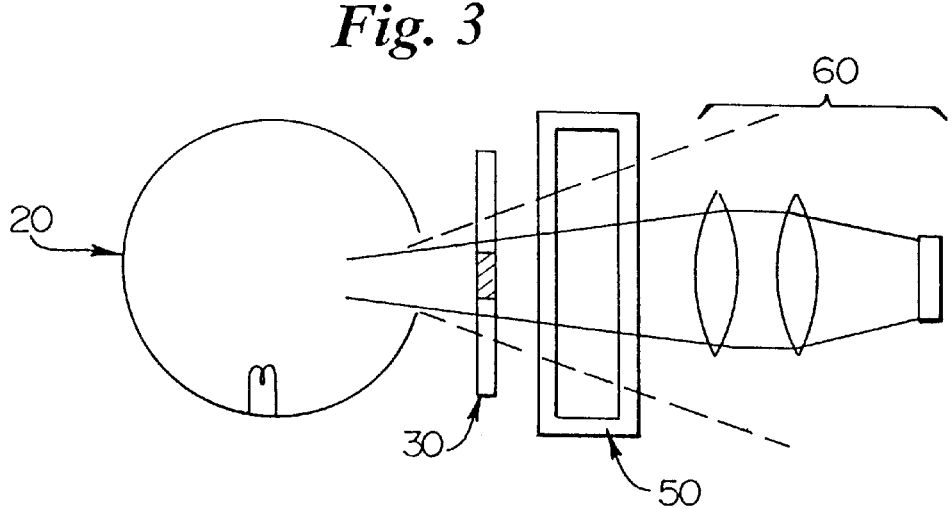
FIG. 3 is a schematic illustration of the analyzer of FIGS. 1 and 2 with the occluder in a third position.

FIGS. 1–3 schematically illustrate an analyzer 10 and a method in accordance with the present invention. The analyzer 10 generally includes a radiation source 20, an occluder 30, a sample holder 50, and a radiation detector 60.

The nature of the radiation source will depend, of course, on the wavelength of the radiation of interest in a particular test. In some circumstances, the radiation source may be a broad-band radiation source with a wide radiation spectrum. In most applications, though, a specific wavelength or several specific wavelengths will be of interest while other wavelengths are of less importance. One could, presumably, configure the detector to respond only to radiation at the desired wavelength(s). In order to simplify the radiation detector, though, one can more carefully select the radiation source to emit a much narrower range of wavelengths to more specifically focus on the wavelength(s) of interest for the test being conducted.

It is desirable that the radiation striking the sample in the sample holder be as uniform across the surface of the sample holder as possible. This can be accomplished in a variety of ways and will depend in large part on the nature of the radiation source. If the radiation source is emitting light in the visible spectrum, for example, one can utilize a plane wave source or can interpose an opalescent filter between the light source and the occluder to create a fairly uniform illumination. Such techniques are well known in the art.

FIGS. 1–3 schematically show a Lambertian light source. Such light sources are well known and need not be discussed in any great detail here. U.S. Pat. No. 4,892,409, the teachings of which are incorporated herein by reference, briefly discusses the use of such a light source in a photometer. Generally, though, common Lambertian sources utilize an internally reflective sphere 22 with a radiation source positioned within the sphere or entering one side of the sphere. The light bounces around the internally reflective sphere, creating a fairly uniform intensity exiting out a side opening 26 in the sphere. In FIGS. 2 and 3, the radiant element 24 is shown as being positioned within the sphere 22. This radiant element should emit radiation at least at the wavelength(s) of interest for the property to be measured.

FIG. 1 illustrates the radiant element as a series of individual diodes 24a, 24b and 24c. A baffle 23 may also be positioned between these diodes and the opening 26 through which light exits the sphere to improve uniformity of the existing light. Any suitable number of diodes may be utilized to generate a radiation profile having desired properties.

If the analyzer 10 is to be used as a hemoglobinometer, for example, at least one of the radiant elements 24a–24d may be a diode emitting light at about 540 nm. In a particularly preferred embodiment, each of the radiant elements 24a–24d is a laser diode emitting light within a rather narrow bandwidth, with each diode emitting a different wavelength. For example, diode 24a may emit at about 650 nm±1 nm, diode 24b may emit at about 660 nm±1 nm, diode 24c may emit at about 685 nm±1 nm, and diode 24d may emit at about 810 nm±1 nm. Such laser diodes are available from a variety of sources.

As is known in the art, selecting a number of different wavelengths of light for use in a hemiglobinometer can allow one to determine not only the total hemoglobin concentration (THb), but also the relative concentrations of the different species of hemoglobin, i.e., reduced hemoglobin or deoxyhemoglobin (RHb), oxyhemoglobin ($O_2$Hb), carboxyhemoglobin (COHb) and methemoglobin (MetHb). The relative absorption of the various species as a function of wavelength is well known. Hence, if one selects four or more wavelengths of light, it is a simple matter to determine the relative concentrations of the species from the measurements taken at those wavelengths. Using these relative concentrations and the measured total hemoglobin concentration, one can determine the total concentration of each species in the sample.

The nature of the occluder will also depend to some extent on the wavelength(s) of the radiation of interest. The occluder desirably permits one to vary both the intensity and the pattern of the radiation striking the sample holder 50. The occluder is desirably configured so that one, by moving the occluder with respect to the radiation source 20, can vary the radiation striking the sample holder in a desired fashion. The occluder is desirably movable between at least three different positions to achieve three different radiation intensities and patterns on the sample holder 50 within the optical path 80 of the system, as described in more detail below.

Figure 4:
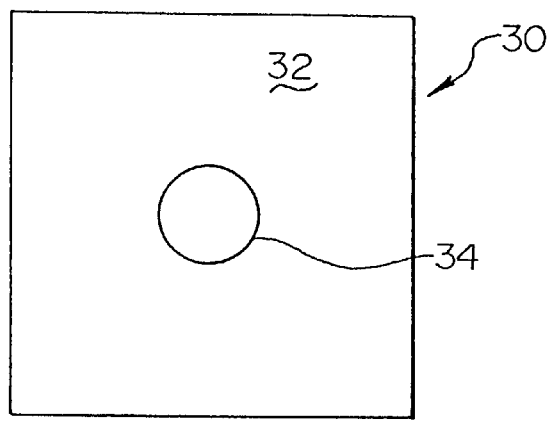
FIG. 4 is a front elevational view of one occluder which can be used in an analyzer of the invention.
Figure 5:
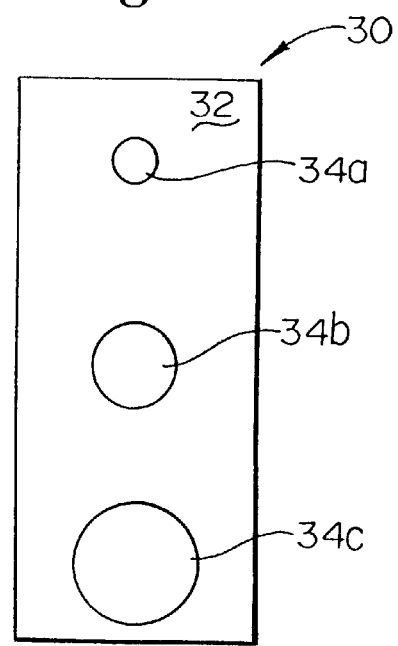
FIG. 5 is a front elevational view of an alternative embodiment of an occluder for use in an analyzer of the invention.
Figure 6:
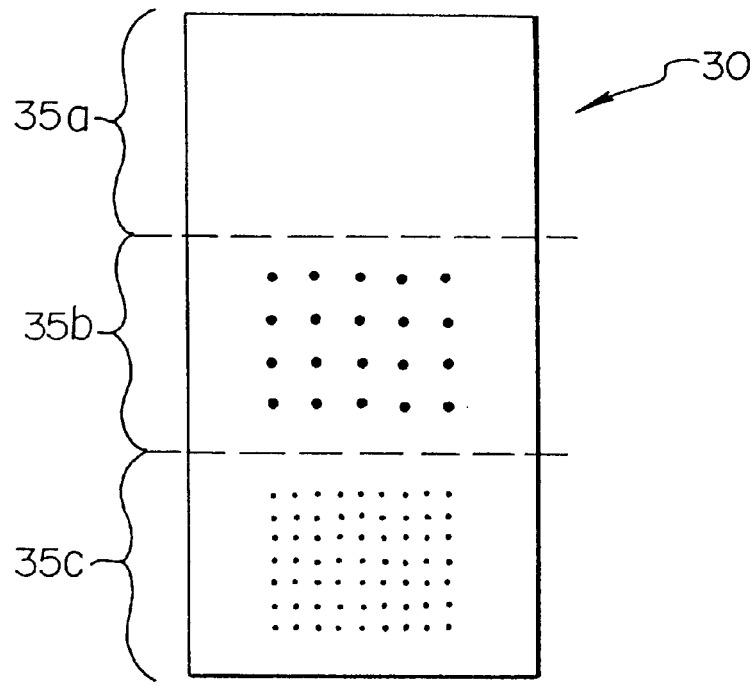
FIG. 6 is a front elevational view of another embodiment of an occluder for use in an analyzer of the invention.

FIGS. 4–6 illustrate three different embodiments of an occluder in accordance with the invention. In the embodiment of FIG. 4, the occluder 30 includes a plate 32 with a single, centrally located occluding dot 34. The nature of the plate and the dot will vary depending on the nature of the radiation being used. If the radiation is a particular wavelength or set of wavelengths of visible light, for example, the plate 32 may comprise a glass plate with a minimal absorption of the wavelength(s) of interest. If so desired, the glass of the plate 32 can be doped with different compounds to yield a filter to further restrict the wavelength(s) of light striking the sample holder 50.

The dot 34 should have a substantial impact on the transmittance of the wavelength of interest when the dot is positioned in the optical path 80 of the analyzer. In a preferred embodiment, the dot is substantially non-transmissive of the relevant wavelengths of radiation. If the occluder 30 is used in a hemoglobinometer, the dot 34 may simply comprise an opaque layer of metal, which should fairly effectively occlude transmission of both visible light and near-infrared radiation.

The relative sizes of the plate 32 and dot 34 can be varied as desired. In carrying out the method described below, it is desirable for the user to be able to readily position the dot 34 out of the radiation path 80. Nonetheless, in order to minimize any unwanted variation in the optical properties of the system, some portion of the plate 32 should be positioned in the radiation path during each of the measurements made by the system. In one embodiment which has been found to work well, a glass plate transmissive of visible light and near-infrared radiation having a centrally positioned dot 34 of metal foil at about ¼ of an inch (about 6.5 mm) in diameter has been found to suffice for use in a hemoglobinometer.

FIG. 5 illustrates an alternative occluder 30 for use with the invention. The occluder of FIG. 4 utilizes a single dot 34 centrally located and, as described more fully in connection with the method below, different fractions of this single dot are positioned within the radiation path in each of the separate readings which are taken. The embodiment of FIG. 5, though, provides a plurality of differently sized occluding dots 34a, 34b and 34c on its surface. The construction of this occluder of FIG. 5 can be substantially the same as that of FIG. 4. The differently sized dots, though, will permit one to centrally locate a different sized dot within the radiation path 80 for each of the measurements taken, with the nature of the radiation striking the sample holder varying accordingly.

Some combination of these two techniques could also be useful in the invention. If one is taking three separate measurements, one can simply provide an occluder with two differently sized dots and one suitably sized area of the plate 32 which does not have a dot. By positioning the area without a dot and the two differently sized dots in the radiation path at different times, one can achieve three different radiation patterns striking the sample.

FIG. 6 shows another alternative embodiment of an occluder 30 in accordance with the invention. Once again, this occluder includes a plate 32 which is highly transmissive of the relevant wavelength(s) of light. Whereas the occluders in FIGS. 4 and 5 utilize no more than one relatively large dot for each position of the occluder, the occluder of FIG. 6 utilizes a different pattern of smaller dots at the three measurement locations 35a, 35b and 35c. In position 35a, the occluder may have no dots applied, i.e., the radiation will pass through just the plate 32. In each of the second and third positions, an array of smaller dots are arranged on the plate 32 at a location where they will be positioned in the optical path 80 of the analyzer when the occluder is in the corresponding position.

The array of dots in the second position 35b is different from the array of dots in the third position 35c. In the illustrated embodiment, the dots in each of these two positions are of about the same size. However, the number of dots in the second position is less than the number of dots in the third position. If so desired, the number of dots can be left substantially the same in the second and third positions, but the sizes of the dots may be different. For example, the dots in the third region 35c may be significantly larger than the dots in the second region 35b. It is believed that both of these approaches would yield the desired effect in carrying out the method of the invention.

Figure 7:
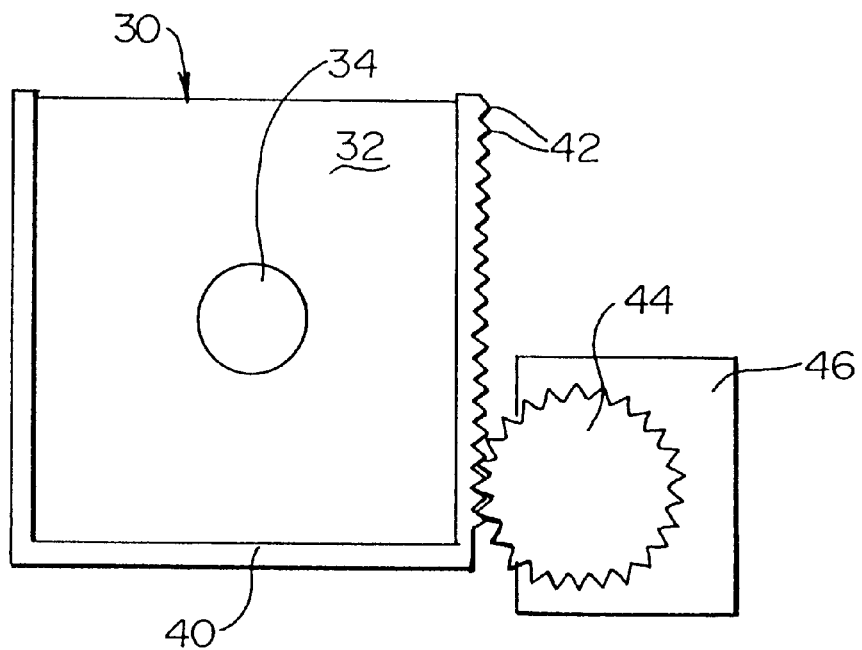
FIG. 7 is a schematic illustration of an occluder and a motor for moving the occluder.

In most embodiments of the invention, the occluder 30 should be movable from one position to another to control the nature of the radiation striking the sample holder 50. FIG. 7 schematically illustrates one simple way of achieving this. The occluder 30 is positioned in a frame 40 which permits one to move the occluder between the different positions. In this schematic drawing, the frame 40 is shown as being connected to a motor 46 by means of teeth 42 on the frame engaging a toothed gear 44 driven by the motor. Any suitable engagement between the motor and the occluder would work equally well. In order to achieve precise position of the occluder for each and every run, the motor may have some positive reference point to define a home position and a precise way of determining the distance traveled. A common stepper motor should serve this function well.

Figure 11:
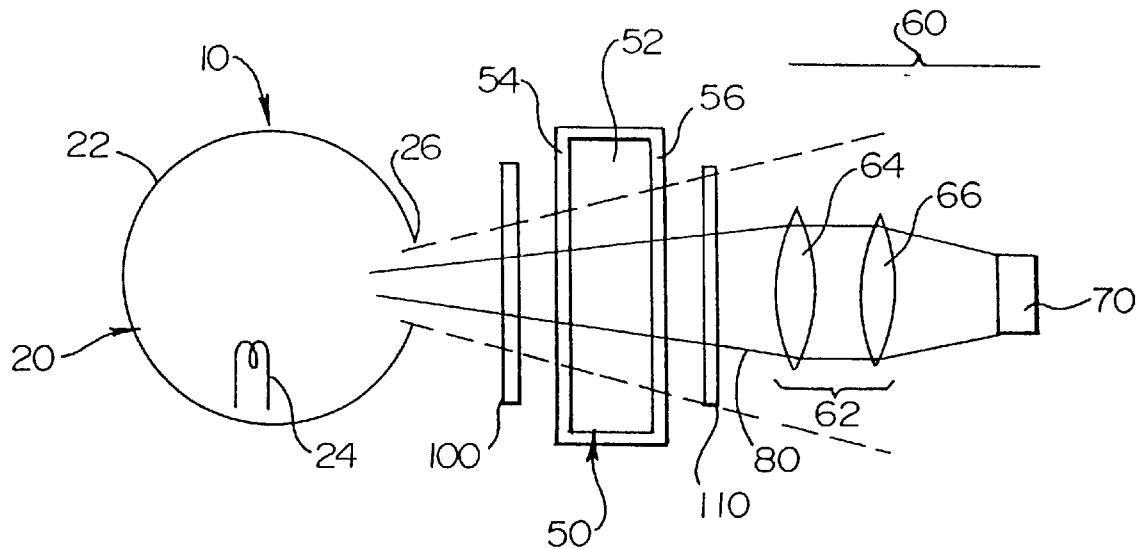
FIG. 11 is a schematic illustration of an analyzer in accordance with an alternative embodiment of the invention.

In an alternative embodiment illustrated in FIG. 11, the occluder may 30 comprise two separate plates. In particular, the occluder of this embodiment comprises two separate polarizing plates 100 and 110 positioned in sequence along the optical path 80 of the light. Each of these polarizing plates desirably includes a polarizing filter; optical quality polarizing glass serving this function is widely commercially available. In the illustrated embodiment, one polarizing plate 100 is positioned between the radiation source 20 and the sample 50 while the other polarizing plate 110 is positioned between the sample and the detector 60.

Changing the relative orientation of the two polarizing plates between three different positions in the manner outlined below would appear to permit functionality similar to that provided by the dots 34 discussed above. There are some differences between these methods (e.g., the dots more directly affect both the total amount of light impinging on the sample in the first place and the dots are minimally affected by optical activity in the sample). Even so, moving these polarizing plates 100 and 110 from one relative position to another can be considered to change the position of the occluder from one position to another in that the percentage of radiation occluded by the occluder will change as the plates are moved from one relative position to another relative position.

The relative positions of the polarizing plates 100 and 110 of the occluder can be altered by simply rotating one of the plates with respect to the other about an axis generally orthogonal to the plates themselves. This can be done by rotating one or both of the plates using a suitable motor. For example, in a first position for taking a first radiation reading, the polarizing plates can be oriented so that their polarizing effects are in phase, permitting virtually all of the light striking the second plate 110 to pass therethrough if there is no change in the orientation of the radiation (e.g., light waves) by the sample. The second plate 110 can then be rotated a predetermined angle (say about 45°) about an axis generally perpendicular to both of the plates 100 and 110 for a second radiation reading. This will occlude a fraction of the radiation which would otherwise pass through the second plate 110 if the sample does not change the orientation of the radiation. If the second plate is rotated again to a different predetermined angle (say a total rotation of about 90° from the first position) for a third reading, the fraction of the radiation occluded for a non-scattering, optically inactive sample will change again.

It is not necessary that one or both of the plates 100 and 110 be rotated with respect to the other. Instead, one of the plates may have three differently oriented polarizing areas (wherein the phase orientation of one polarizing area differs from the phase orientation of the two other polarizing areas) and the plate can be moved vertically as discussed in connection with FIG. 7.

Figure 12:
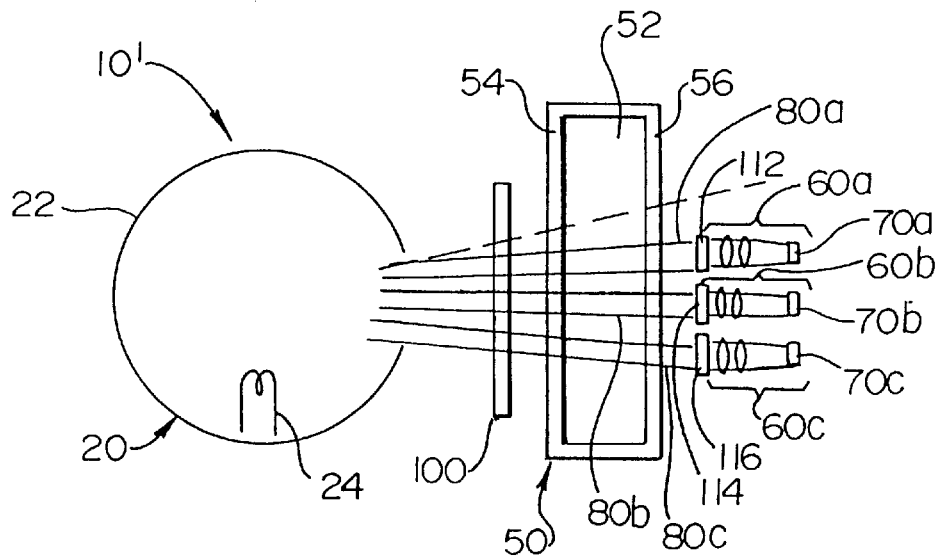
FIG. 12 is a schematic illustration of an analyzer in accordance with yet another alternative embodiment of the invention.

FIG. 12 illustrates an analyzer 10' in accordance with another alternative embodiment of the invention. In this alternative analyzer 10', there is no need to move a polarized plate. There is a stationary first polarizing plate 100, similar to the analyzer of FIG. 11. However, instead of a moveable second polarizing plate 110, there are three different polarizing plates 112, 114 and 116 through which light passes after passing through the sample. One of the polarized plates is associated with each of three separate detectors 60a, 60b and 60c. By orienting the phases of the three polarized plates at different relative orientations to the first polarizing plate 100, one can obtain three measurements taking into account three different light paths 80a, 80b and 80c. It is believed that such an arrangement would permit one to collect data to be used in accordance with the invention (with each of the three detectors being used to take one of the readings $T_1$, $T_2$ and $T_3$ discussed below) without having to physically move a plate from one measurement position to another.

The sample holder 50 should be designed to hold samples of the type being measured in the analyzer 10. If these samples are solid, the sample holder can simply comprise a frame or jig for holding the samples in a precise location. If the sample is a liquid, though, the sample holder 50 can comprise a vial or cuvette. In a preferred embodiment, the vial or cuvette is removable so that it can be discarded after use with a single sample to minimize the risk of cross-contamination.

The vial or cuvette 50 desirably has a fluid-receiving well 52 defined between two precisely spaced-apart walls 54 and 56. These walls should be highly transmissive of the wavelengths of radiation of interest. The space between the walls 54, 56 will essentially define the relevant path length of radiation passing through the sample, at least if the sample is non-scattering. Since variations in this path length can have a significant impact on the measured transmittance, it is important to ensure that the space between the walls 54 and 56 remain substantially the same from one measurement to another. The exact distance between the two plates is not as relevant as is the consistency of this measurement from one vial or cuvette to the next.

At least a portion of the radiation passing through the sample holder 50 is collected in a radiation detector 60. The radiation detector will vary with the nature of the radiation source 20. For example, the radiation detector may include a lens set 62 for directing visible light on a photomultiplier tube, photodiode or similar detector 70. In the illustrated embodiment, the lens set includes two lenses 64, 66. Any suitable number of lenses which will serve to direct the desired cone of light onto the detector to accurately define a specific radiation path 80 will suffice.

One can vary the arrangement of the lens set 62 and the area of the sample holder 50 on which the lens set focuses the detector. One potential source for error, though, is radiation traveling through the sample holder itself. It is possible for light, for example, to propagate through the sides of the sample holder, going from one side of the holder to the other without passing through the sample. Although this can be handled, at least in part, by making the sidewalls opaque, one could instead focus the lens set 62 to image an area of the sample holder spaced from the sides of the sample holder onto the detector to minimize the impact of this anomaly.

As noted above, the present invention provides a method for measuring radiation absorption of a sample which may or may not scatter that radiation. In a particularly preferred embodiment, the method will permit one to determine both the nature of the scattering, if any, caused by the sample and the impact of that scattering on the total transmission measurements.

For purposes of convenience, the method of the present invention will be discussed in connection with the analyzer illustrated in FIGS. 1–7. It should be understood, though, that these drawings are simply used for purposes of convenience and that other, different analyzer configurations may also be used in accordance with the present method.

Figure 8:
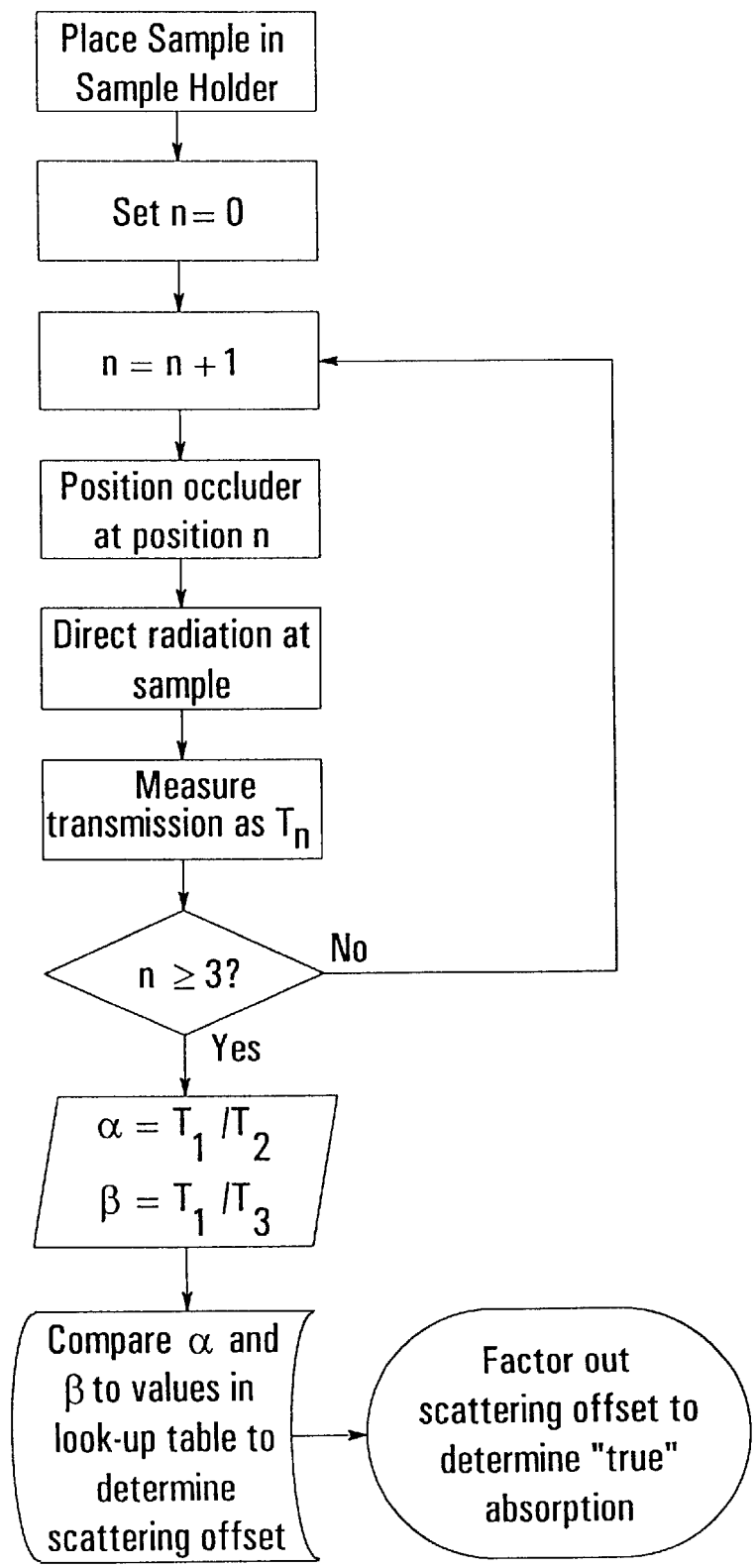
FIG. 8 is a flow chart schematically illustrating a method in accordance with one embodiment of the invention.

FIG. 8 schematically illustrates an embodiment of a method of the invention. In accordance with this method, a sample is placed in the sample holder 50. The sample holder is positioned along the radiation path 80 so that radiation emitted by the radiation source 20 will be directed through the sample and the transmitted radiation will be detected by the radiation detector 60.

A series of transmittance measurements are then taken. In the schematic flow chart of FIG. 8, an indexing number n is initially set at 1. The occluder is then positioned at the corresponding position, i.e., its first position. In the embodiment illustrated in FIG. 1, this would comprise positioning the occluder 30 shown in FIG. 4 with the centrally located dot 34 positioned generally outside the radiation path 80. The radiation will pass through the glass plate 32, but the dot will have no impact on the nature of the radiation striking the sample in the sample holder 50.

Once the occluder is positioned in its first position, radiation is directed at the sample from the radiation source 20 along radiation path 80. The intensity of the radiation passing through the sample and collected by the radiation detector 60 is then measured and recorded as the first radiation measurement $T_1$. In the case of a hemoglobinometer, this would comprise measuring the transmittance of the relevant wavelength(s) of light, such as measuring the intensities of 650 nm, 660 nm, 685 nm and 810 nm light sources passing through the sample.

Once the first transmission measurement is recorded, the process is repeated, with the indexing indicator n being incremented by 1. The occluder is then positioned at the second position. As illustrated in FIG. 2, if the occluder 30 of FIG. 4 is used, a portion of the dot 34 may be positioned in the radiation path 80, with another portion of the dot 34 positioned outside. In the schematic illustration of FIG. 2, about half of the dot is included within the radiation path while about half of the dot is positioned outside.

Once the occluder is in position, the radiation will once again be directed at the sample and a second measurement will be taken with the radiation detector. This second measurement will be recorded as the second radiation measurement $T_2$.

This process is then repeated at least one more time. In the embodiment illustrated in FIG. 3, the dot 34 is positioned entirely within and generally centered along the axis of the radiation path 80. Radiation from the radiation source 20 is again directed at the sample and a third radiation measurement $T_3$ is recorded. In one embodiment which has been found to work well, the dot 34 is only slightly smaller than the cross-sectional area of the cone of radiation emanating from the source at the point where the occluder 30 is positioned. This will still allow a halo of radiation to strike the sample, which will tend to further accentuate the effects of scattering on the radiation measurement $T_3$.

In recording the first, second and third radiation measurements, one can take a single measurement with the radiation detector for a fixed period of time. In a preferred embodiment, though, each of the first, second and third radiation measurements is actually an average of a number of individual measurements. If the radiant element 24 comprises a light emitting laser diode, 24a, for example, one can pulse such a diode for short periods of time. In one preferred embodiment, the laser diode is pulsed at least about 10 times during the course of each "measurement". The ten resulting readings can then be averaged together to produce the "measurement". If a plurality of radiant elements at different wavelengths (e.g., diodes 24a–24d) are used, each element desirably radiates at a different time so that at least one separate measurement can be taken for each element at each occluder position.

FIG. 8 is based on an assumption that a total of three separate radiation measurements will be taken. While at least three radiation measurements should be taken in accordance with the present method, one could take more radiation measurements at different positions of the occluder, simply by repeating the loop, as outlined above (i.e., by changing the decision "n≧3?" in FIG. 8 to "n≧4?", "n≧5?", etc.).

The differences in the position of the occluder in each of the three measurements yields a different radiation pattern impinging on the sample holder 50. (In the embodiments of FIGS. 11 and 12 using polarizers, the occluder instead differently conditions the light impinging on the sample holder and passing through to the detector, but these two polarizer-based systems are believed to provide similar functionality, as noted above.)

In the first position illustrated schematically in FIG. 1, the full intensity of the radiation is directed against the sample holder and this intensity is desirably substantially uniform across the entire surface of the sample holder. In the second position illustrated in FIG. 2, the occluder will occlude a portion of the radiation impinging on the sample. The dot not only reduces the intensity of the radiation striking the sample holder, but also changes the relative intensities of the radiation striking different areas of the sample holder. In the third position illustrated in FIG. 3, the occluder 30 will have the dot 34 substantially entirely within, and perhaps generally centered along the axis of, the radiation path 80. This will further change both the total intensity of the radiation impinging on the sample holder 50 and the relative intensity of the radiation across the surface of the sample holder.

Changing both the intensity of the radiation striking the sample and the relative intensity of the radiation over the surface of the sample will change the relative impacts of true absorption effects of the sample and the scattering effects of the sample. For example, when the dot 34 is substantially centered within the radiation path, as illustrated in FIG. 3, the amount of light which would be directly transmitted through the sample will be reduced while the effects of scattering on the total measured transmittance will be augmented. Stated another way, the effect of light being scattered from the peripheral portions of the sample in FIG. 3 will become a more prominent fraction of the total radiation impacting on the detector 60 than when the occluder is in the position shown in FIG. 1.

As noted above, the embodiments of FIGS. 11 and 12 do not employ any occluding dots. Instead, the occluder comprises at least two polarizing plates. In the analyzer of FIG. 11, the light is polarized as it passes through the first polarizing plate 100, i.e., the polarizing plate will permit only light waves with a certain range of angular orientations to pass therethrough, reflecting the rest of the light waves. The polarized light then passes through the sample and impinges on the second polarizing plate 110. If the first and second polarizing plates are in phase with one another and the sample is neither scattering nor optically active, essentially all of the light striking the second polarizing plate 110 will pass therethrough. By changing the relative orientation of the first and second plates (i.e., by varying the phase relationship of the two plates), one will reduce the amount of light transmitted through the second polarizing plate if the sample is neither scattering nor optically active. When the phase relationship between the two plates is about 90°, very little light (in theory, no light at all) will pass through the second polarizing plate for such a sample.

Light passing through a scattering sample will be scattered in different directions along the optical path. As a result, the polarized light striking the sample will no longer be neatly oriented with the second polarizing plate 110 by the time it strikes that plate. As a result, less of such scattered light will pass through the second polarizing plate and strike the detector 60 when the two plates 100 and 110 are in phase with one another and more light will pass through the second plate when the two plates are oriented 90° out of phase. If the sample is sufficiently scattering, the light exiting the sample and striking the second polarizing plate will be essentially randomly oriented. As a result, the amount of light passing through the second polarizing plate 110 will remain substantially the same regardless of its orientation with respect to the first plate 100. Consequentially, a comparison of the relative intensities of the first, second and third radiation measurements taken using the embodiment of FIG. 11 will give some indication of the degree to which the sample scatters light.

The first, second and third radiation measurements (regardless of what embodiment of an analyzer is employed) can be thought of as comprising two separate effects of the sample on the radiation. One of these effects is the "true"

absorption, while the other is a scattering effect. As used herein, the "true" absorption of the sample is the absorption level one would observe if the sample were non-scattering and the light were simply to traverse the sample in a relatively straight-forward manner.

As used herein, the term "scattering effects" is used to refer to a sum of the impacts on the measured transmittance caused by the scattering particles. Some radiation will fail to reach the detector 60 due to back scattering of the radiation in a direction away from the detector, such as out the sides of the sample holder or back toward the illumination source. In addition, the "scattering effects" include the often substantial increase in absorption by the sample attributable to the increased mean path length of light therethrough as it bounces from particle to particle on the way to the detector 60. If the embodiment of FIG. 11 or FIG. 12 is used, the "scattering effects" will also include a randomization of the orientation of the previously polarized light striking the sample.

In order to determine the relative impacts of scattering and absorption, the first, second and third radiation measurements are compared to one another. In particular, two ratios are determined. The first ratio, referred to as "$\alpha$", is the ratio of the first radiation measurement $T_1$ to the second radiation measurement $T_2$. The other ratio, referred to as "$\beta$", is the ratio of the first radiation measurement $T_1$ to the third radiation measurement $T_3$. Hence, $$\alpha = \frac{T_1}{T_2} \qquad \beta = \frac{T_1}{T_3}$$

If more than three measurements are taken, additional ratios can be calculated. Presumably, each of these ratios would involve comparing the first transmission measurement to another measured transmittance ratio (i.e., $\chi=T_1/T_4$, $\delta=T_1/T_5$, etc.). Such additional measurements and calculations are not believed to be necessary. While additional measurements may further increase the accuracy of the device by providing additional reference points, such reference points are not believed to be necessary and taking the measurements would likely increase processing time for each sample and reduce the throughput of the device.

Once the values of $\alpha$ and $\beta$ have been determined, they can be compared to a look-up table of $\alpha$ and $\beta$ values. The look-up table will correlate the calculated $\alpha$ and $\beta$ values to specific contributions to optical density from the scattering effects, i.e., the value of S in FIG. 10. The scatter effects can then be mathematically factored out of the transmission measurements to achieve the "true" absorption measurement for the sample.

The formula for the transmittance of a sample can be stated as follows:

Transmittance=absorption transmission×scattering transmission

One can use the look-up table to determine the specific contributions to the transmittance from the scattering effects, i.e., the "scattering transmission". For example, if one were to determine that scattering causes a transmission loss of 20%, the scattering transmission in the above formula could be stated as 0.80. As a consequence, one can determine the "true" absorption of a particular sample simply by dividing the measured transmittance by the determined scattering transmission.

The look-up table can be created by measuring a series of samples having known absorption values and storing the $\alpha$ and $\beta$ values for those samples in the table. By comparing the $\alpha$ and $\beta$ values for a particular sample to the previously collected measurements in the table, one should be able to reasonably accurately match up the sample with a known reference. To the extent the measured values fall between the readings in the table, one may be able to interpolate between the table entries to further refine the precision of the measurement without greatly sacrificing accuracy.

Even with fairly tight manufacturing tolerances, there will be some variability between the optical parameters from one machine to the next. One could measure the entire set of samples and generate a new look-up table for each individual machine. In most circumstances, though, such a long process should be unnecessary if the manufacturing tolerances are sufficiently tight. Instead, one can simply measure a smaller number, such as three or four, samples having known optical properties for each machine and use those measurements to calibrate the machine. Such calibration can be mechanical (e.g., by adjusting optical parameters) or incorporated in the calculation process (e.g., by incorporating a calibration/correction factor into software used to process the data collected).

Figure 9:
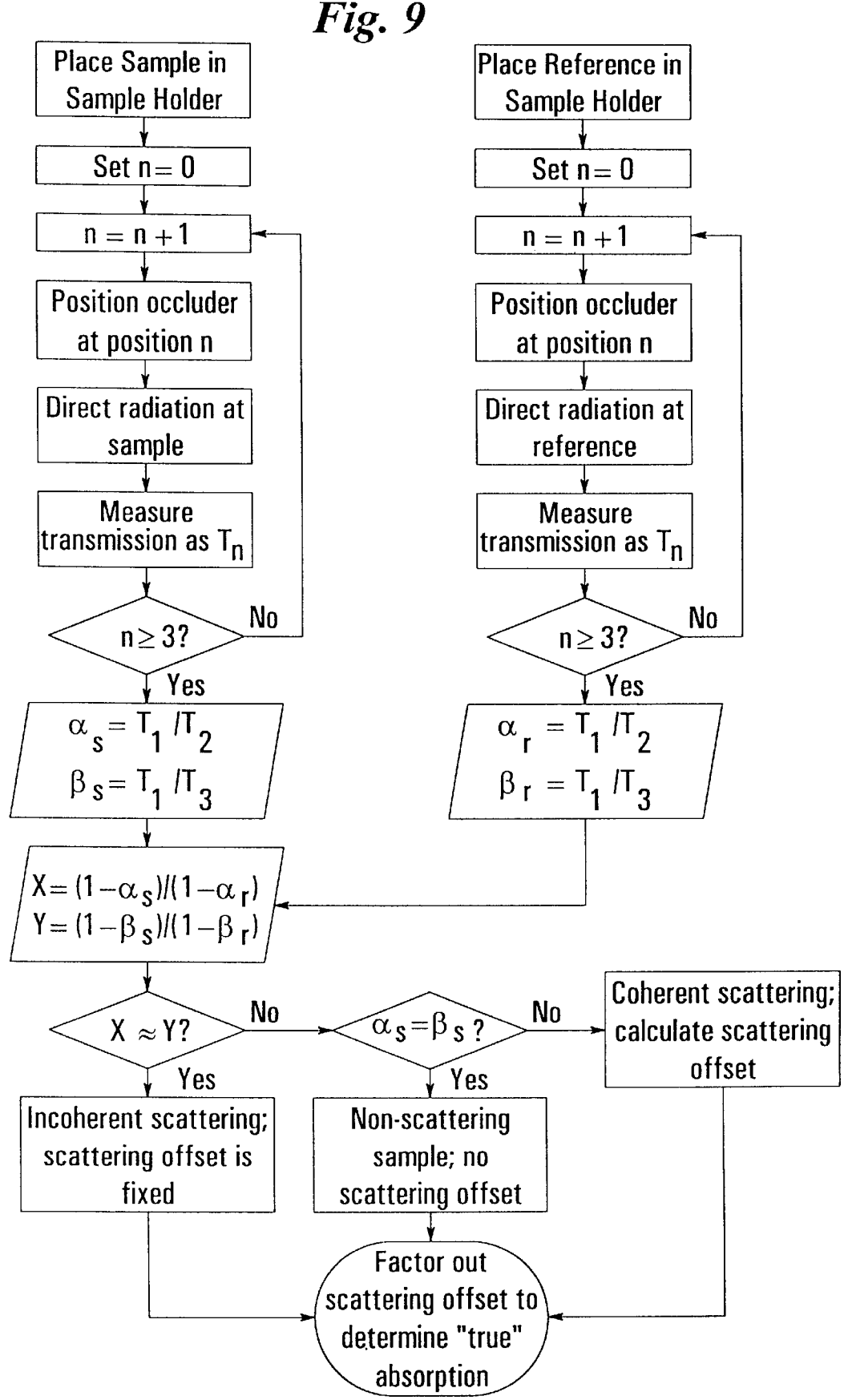
FIG. 9 is a flow chart schematically illustrating another method in accordance with the invention.

In a further embodiment of the invention, illustrated in FIG. 9, the method also employs a separate set of reference measurements to which the above $\alpha$ and $\beta$ values are compared. As shown in FIG. 9, essentially the same measurement process is carried out on the sample—the sample is placed in the sample holder and at least three measurements ($T_1$, $T_2$ and $T_3$) are taken with the occluder at different positions and the values of $\alpha$ and $\beta$ can be calculated. Much the same thing is done again with a reference standard replacing the sample in the sample holder, yielding three different measurements and reference values for $\alpha$ and $\beta$. To distinguish the ratios calculated for the sample from the reference ratios, the sample ratios are designated $\alpha_S$ and $\beta_S$ while the reference ratios are designated $\alpha_r$ and $\beta_r$.

The reference measurements can be taken before or after the measurements for the sample. The reference measurements will be needed to calculate the final results for the sample as detailed below, though. To save time, one can take the reference measurements once for comparison to transmission measurements for a number of different samples. Although the reference measurements should be taken periodically to make sure the device is properly calibrated, the reference measurements should not change substantially over time without significant changes in the measuring device. If there are significant changes, such as significant temperature variations, a change in the light source, etc., collecting a new set of data for the reference standard should allow one to correct for such variations, as discussed below.

The reference standard can be formed of a variety of materials. The primary purpose of the reference is to define a standard to which sample measurements can be compared. It is preferred that the reference standard behave in a manner similar to a sample which scatters the source radiation so the nature of the sample's scattering can be compared to the nature of the reference standard's scattering. The reference can simply comprise a fluid of a known composition and having known properties placed in a standard sample holder. Care should be taken to ensure that the scattering particles are suitably suspended in the liquid to ensure that the reference will yield the expected results.

In one preferred embodiment which has particular utility for use in connection with a hemoglobinometer, the reference standard is instead a blank formed of Delrin, a trade name for a commonly available translucent acetal resin commercially available from a number of sources. Delrin scatters radiation in the visible and near infrared regions in a manner similar to the manner in which red blood cells in a blood sample scatter such radiation. Instead of placing a reference fluid in a standard sample holder, the Delrin reference can comprise a solid blank having about the same shape and size as the sample holder. This will help ensure that the reference standard remains stable not only during a single set of readings $T_1$, $T_2$ and $T_3$, but will also yield predictable, reproducible results from one run to the next.

Once the transmission measurements have been taken for both the sample and the reference standard, the results for these two sets of data can be compared. The goal of this comparison is to determine at least the nature of the scattering of the sample, i.e. whether it is coherent or incoherent, and, ideally, also to determine the effects of the scattering on the transmission measurements for the sample. The comparison can be conducted in any manner which will achieve this end. One comparison which has been found useful compares the values X and Y calculated as follows:

$$X = \frac{1-\alpha_s}{1-\alpha_r} \qquad Y = \frac{1-\beta_s}{1-\beta_r}$$

Both X and Y involve a comparison of the behavior of the sample to the behavior of the reference when subjected to the same radiation, i.e. when the occluder is in the same relative positions. The variable X involves a comparison of the effects of the occluder in its second position on the transmission measurements for the sample and the reference standard; the variable Y involves a comparison of the effects of the occluder in its third position on the transmission measurements for the sample and the reference standard.

One can calculate a third variable Z as X−Y. If X and Y are the same, i.e., Z=0, the sample is scattering in much the same fashion as is the reference. Ideally, X and Y would be identical, but in reality there will be some natural variability in these measurements. Hence, if X is approximately the same as Y, i.e., Z is relatively small, one can still make the same assumption. As a result, if X and Y are approximately the same and the reference standard behaves as an incoherently scattering sample, the sample must be incoherently scattering. As the effects of incoherent scattering are substantially constant, one can assume that the scattering offset (S in FIG. 10) is a fixed value and factor that fixed optical density offset out of the transmission results to determine the "true" absorption for the sample as outlined above.

If X and Y are different and the reference standard behaves as an incoherently scattering sample, one can presume that scattering is not incoherent, but that does not necessarily dictate that the sample is scattering coherently. In particular, if the values $\alpha_S$ and $\beta_S$ for the sample are approximately the same despite the differences in the light pattern striking the sample at the second and third positions, this indicates that the sample is essentially non-scattering and that the scattering offset S for the sample should be zero.

Figure 10:
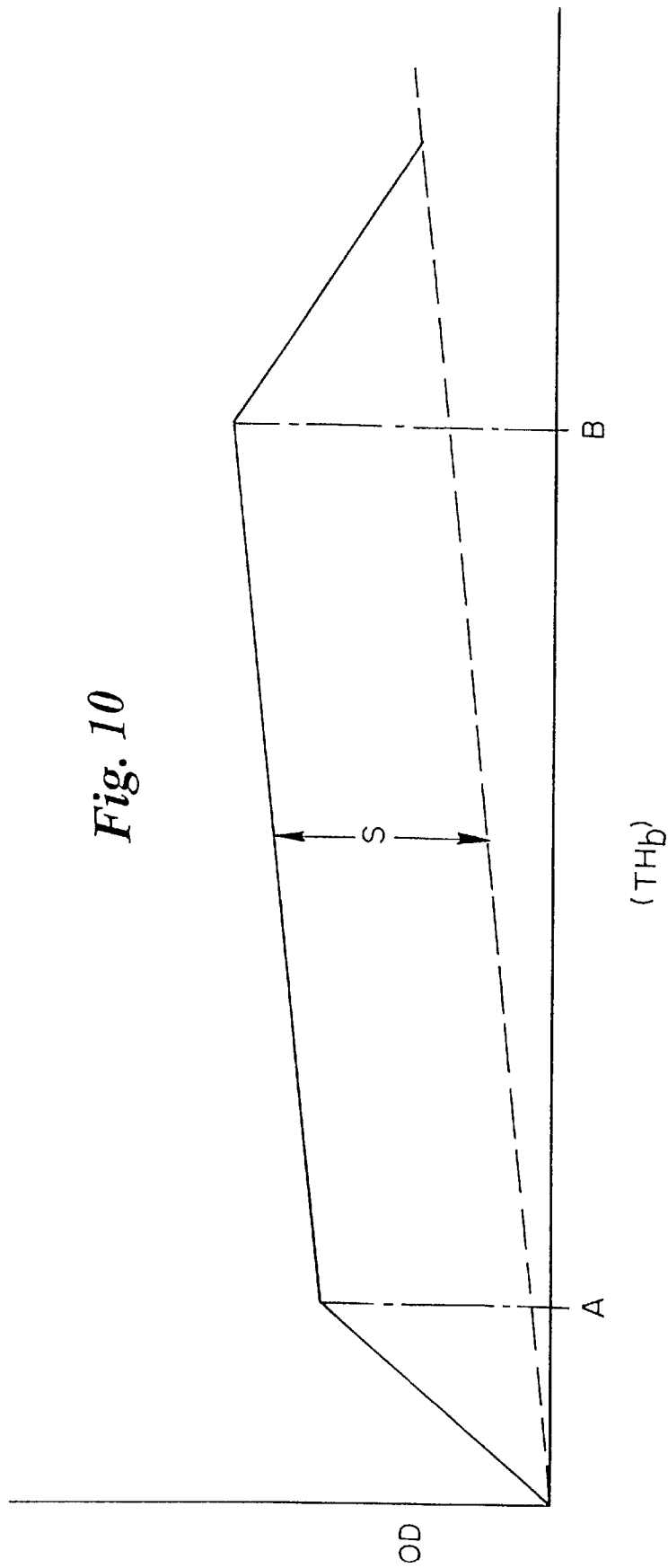
FIG. 10 is a graph schematically illustrating the relationship between the optical density of a sample and the total hemoglobin concentration of the sample.

Finally, if the sample is determined to be scattering (i.e. $\alpha_S \neq \beta_S$) and is not incoherently scattering, it must be coherently scattering, i.e. it is less than A or greater than B in FIG. 10 if the sample is whole blood. As discussed above, the effects of coherent scattering on transmittance measurements will vary depending on the magnitude of the scattering effect. (This will depend on the concentration of the scattering particles in the sample, among other factors.)

One can define a ratio A of the measured transmission of the sample to the variable Z noted above, i.e. the difference between the values X and Y. it has been determined that there is a fairly linear relationship between the hematocrit and this ratio A.

EXPERIMENTAL EXAMPLE

To demonstrate the effectiveness of the present invention in accurately measuring absorption for scattering samples, a series of measurements were taken in accordance with the method and the results of those measurements were compared to the measurements made using a standard, commercially available analyzer. An analyzer constructed essentially as described above in connection with FIG. 1 was provided. The light source comprised an internally reflective sphere 22 with four separate laser diodes 24a–24d. The sphere was purchased from Labsphere, Inc. of North Sutton, N.H., USA as number CA-03122-000 CSTM-IS-030-SF. This sphere is a 3-inch internally reflective sphere with an internal baffle.

Although further details are available from the manufacturer, the sphere generally comprised two spun aluminum hemispheres joined to one another. The interior of each hemisphere was coated with Spectraflect™, a white, highly reflective coating which exhibits lambertian properties. The assembled sphere had three ports, each of which had an inner diameter of about one inch (about 2.5 cm). Two of the ports were diametrically opposite one another while the third was located about 90° from each of the other ports. One of the opposed ports served as a light inlet while the opposite port was plugged with a reflective plug. The third port served as the side opening 26 through which light exited the sphere. A reflective baffle extended radially inwardly from the inner surface of the sphere at a location between the light inlet and the third port.

Four laser diodes were positioned adjacent the light inlet. These diodes emitted light at 650 nm, 660 nm, 685 nm and 810 nm. The first three were purchased from Toshiba as model numbers TOLD 9412, TOLD 9321 and TOLD 9111, respectively. The 810 nm laser diode was Sharp model number LT010MD.

The occluder 30 comprised a 2 inch by 2 inch (5.08 cm×5.08 cm) glass plate 32 with a single dot 34 formed of chrome vacuum deposited on the plate, yielding a dot which had an optical density of 4 or greater across a wavelength range of 600–1100 nm. The dot was about 0.209 inches (about 5.31 mm) and was centered on the glass plate. The plate and the dot were overcoated with layer of silicone monoxide and both sides of the plate were coated with an antireflective layer.

The occluder was positioned about 0.1 inches (about 2.5 mm) from the side opening 26 in the sphere. The position of the occluder was controlled by a stepper motor 46 which was originally designed for use in moving the head of a hard disc drive of an electronic data storage system.

The sample holder 50 was a disposable cuvette formed of acrylic. The walls 54, 56 of each cuvette were each about 0.050 inches (about 1.27 mm) thick and were spaced from one another about 0.048 inches (about 1.22 mm). Each sample being measured in the system was placed in a fresh cuvette. The reference standard comprised a blank of translucent white Delrin which was about 0.14 inches (about 3.6 mm) thick where light passes therethrough and its external dimensions were similar to those of the cuvettes to enable it to be readily used in place of the cuvettes in the analyzer.

The radiation detector 60 comprised a 6DP silicon photodiode purchased from United Detector Technology. A pair of lenses focused the radiation detector on an area of about 0.25 inches (about 6.4 mm) in diameter on the back wall 56 of the cuvette.

An initial set of "air" measurements was taken with no sample in the sample holder. With the occluder in the first position (where the glass plate was positioned within the cone of light emanating from the source, but the dot was positioned outside the cone), intensity measurements were taken for each diode 24a–24d and a fifth measurement was taken with no light source at all (to measure stray or background light in the system). A series of at least 10 measurements were taken for each light source and these measurements were averaged together to yield a first intensity measurement for the occluder's first position for each light source.

The occluder was then moved into a position where the dot 34 was positioned about half in the cone of light emanating from the source and about half outside that cone. A second set of five measurements (one with no active light source and one for each light source) were taken with the occluder in this position, with each measurement being an average of at least 10 individual measurements. Finally, the occluder was moved into a third position wherein the dot was entirely encompassed within and substantially centered in the cone of light. A third set of five averaged measurements were then taken.

A sample holder was then filled with distilled water and the sample holder was placed between the occluder and the radiation detector. The occluder was positioned in the first position described above and a set of five averaged intensity measurements were taken. The same was then done with the occluder in the second position to generate a second set of intensity measurements and in the third position to generate a third set of intensity measurements.

The sets of intensity measurements were used to calculate the transmittance of the distilled water sample at each wavelength. In a known fashion, the transmittance of the sample at each wavelength in the first set of measurements was calculated by subtracting the background (no light) measurement from the first set of measurements and dividing that result by the analogous number for the air measurement. This yielded a $T_1$ transmittance measurement for each wavelength. The same was done to generate $T_2$ and $T_3$ transmittance measurements from the second and third sets of intensity measurements, respectively. Finally, the values of $\alpha_s$ and $\beta_s$ were calculated for each wavelength. These $\alpha_s$ and $\beta_s$ values, as well as the various sets of intensity measurements and the $T_1$, $T_2$ and $T_3$ measurements are listed in Table 1:

TABLE 1

| Measurement | LIGHT SOURCE | | | | |
|---|---|---|---|---|---|
| | No Light | 650 nm | 660 nm | 685 nm | 810 nm |
| AIR | | | | | |
| NO DOT | 0.0115 | 0.8483 | 0.8637 | 0.8775 | 0.9173 |
| PARTIAL DOT | 0.0115 | 0.4843 | 0.4927 | 0.5006 | 0.5285 |
| FULL DOT | 0.0129 | 0.2553 | 0.2591 | 0.2631 | 0.2757 |
| DISTILLED H₂O | | | | | |
| NO DOT | 0.0119 | 0.7824 | 0.7979 | 0.8123 | 0.8491 |
| PARTIAL DOT | 0.0119 | 0.4534 | 0.4617 | 0.4704 | 0.4964 |
| FULL DOT | 0.0135 | 0.2396 | 0.2435 | 0.2479 | 0.2598 |
| TRANSMITTANCE | | | | | |
| $T_1$ | | 0.92081 | 0.92235 | 0.92433 | 0.92439 |
| $T_2$ | | 0.93375 | 0.93493 | 0.93743 | 0.93722 |
| $T_3$ | | 0.93294 | 0.93419 | 0.93684 | 0.93722 |
| $\alpha_s$ | | 0.98614 | 0.98654 | 0.98602 | 0.98632 |
| $\beta_s$ | | 0.987 | 0.98732 | 0.98665 | 0.98632 |

As can be seen from these results, the transmittance values were relatively high, as one would expect for distilled water. The values of $\alpha_s$ and $\beta_s$ were fairly close to one another. This indicates that the sample behaves about the same regardless of the fact that the light source may be significantly less direct when the occluder is in one position (e.g., the second position) than it is in another (e.g., the third position). As distilled water is non-scattering, this bears out the anticipated relationship between $\alpha_s$ and $\beta_s$ for such a sample.

Next, the transmittance of the Delrin reference standard discussed above was measured. In a manner directly comparable to that used above in connection with the distilled water sample, sets of intensity measurements were taken both in air and with the reference standard in place of the sample holder. The values of $T_1$, $T_2$ and $T_3$ for the reference standard were calculated. These values were then used to calculate $\alpha_r$ and $\beta_r$ for the reference in accordance with the formulas set forth above. The intensity measurements, as well as the calculated values for $T_1$, $T_2$, $T_3$, $\alpha_r$ and $\beta_r$ for each wavelength are listed in Table 2.

TABLE 2

| Measurement | LIGHT SOURCE | | | | |
|---|---|---|---|---|---|
| | No Light | 650 nm | 660 nm | 685 nm | 810 nm |
| AIR | | | | | |
| NO DOT | 0.0130 | 0.8666 | 0.8742 | 0.8927 | 0.9149 |
| PARTIAL DOT | 0.0130 | 0.3808 | 0.3839 | 0.3920 | 0.4072 |
| FULL DOT | 0.0155 | 0.2261 | 0.2276 | 0.2319 | 0.2334 |
| DELRIN STANDARD | | | | | |
| NO DOT | 0.0131 | 0.0616 | 0.0620 | 0.0644 | 0.0667 |
| PARTIAL DOT | 0.0131 | 0.0420 | 0.0422 | 0.0438 | 0.0462 |
| FULL DOT | 0.0155 | 0.0376 | 0.0378 | 0.0388 | 0.0416 |
| TRANSMITTANCE | | | | | |
| $T_1$ | | 0.06162 | 0.06152 | 0.06302 | 0.06422 |
| $T_2$ | | 0.08423 | 0.08408 | 0.08633 | 0.08969 |
| $T_3$ | | 0.11234 | 0.11264 | 0.11473 | 0.1274 |
| $\alpha_r$ | | 0.73162 | 0.73167 | 0.72996 | 0.71604 |
| $\beta_r$ | | 0.54854 | 0.54615 | 0.54931 | 0.50413 |

A blood sample having a known hematocrit fraction (Hct) of about 0.10 was prepared. The sample was prepared by spinning down a dog blood sample to separate the plasma and pack down the red blood cells. The plasma and the packed red blood cells were then mixed together at a ratio of about 9:1, to yield a sample with a fractional volume of red blood cells of about 10%, i.e., Hct=0.10. A volume of this prepared sample was placed in a fresh sample holder and the sample holder was placed in the analyzer. This sample was subjected to the same measurement process as was carried out on the distilled water sample and the Delrin reference standard. The resulting values of $T_1$, $T_2$, $T_3$, $\alpha_s$ and $\beta_s$ are shown in Table 3. (The sets of intensity measurements have been omitted solely in the interest of brevity.) In addition, the values of X and Y were calculated using these $\alpha_s$ and $\beta_s$ values and the values of $\alpha_r$ and $\beta_r$ obtained from the Delrin reference standard and listed in Table 2 above.

TABLE 3

| Measurement | LIGHT SOURCE | | | |
|---|---|---|---|---|
| | 650 nm | 660 nm | 685 nm | 810 nm |
| $T_1$ | 0.09285 | 0.09456 | 0.09908 | 0.08689 |
| $T_2$ | 0.11016 | 0.11150 | 0.11808 | 0.10225 |
| $T_3$ | 0.11683 | 0.11921 | 0.12556 | 0.11007 |

TABLE 3-continued

| Measurement | LIGHT SOURCE | | | |
| --- | --- | --- | --- | --- |
| | 650 nm | 660 nm | 685 nm | 810 nm |
| $\alpha_S$ | 0.84282 | 0.84802 | 0.83908 | 0.84984 |
| $\beta_S$ | 0.79471 | 0.79319 | 0.78905 | 0.78946 |
| X | 0.586 | 0.566 | 0.596 | 0.529 |
| Y | 0.455 | 0.335 | 0.468 | 0.425 |
| Z = \|X − Y\| | 0.131 | 0.111 | 0.128 | 0.104 |

As can be seen from Table 3, this yielded X and Y values which are fairly different—at each wavelength, Z was at least 20% of Y. As these values clearly are not approximately the same, one can tell that the sample is not incoherently scattering. Furthermore, since $\alpha_S$ and $\beta_S$ are not approximately the same, one can tell that the sample does scatter, so the scattering must be largely coherent in nature.

The same procedure was carried out on one sample having a known Hct of about 0.20 and another sample having a known Hct of about 0.30. The values of $T_1$, $T_2$, $T_3$, $\alpha_S$ and $\beta_S$ are shown in Tables 4 and 5, respectively. As can be seen from both of these samples, the values of X and Y are approximately the same.

TABLE 4

| Measurement | LIGHT SOURCE | | | |
| --- | --- | --- | --- | --- |
| | 650 nm | 660 nm | 685 nm | 810 nm |
| $T_1$ | 0.06606 | 0.0684 | 0.07226 | 0.05204 |
| $T_2$ | 0.07966 | 0.08275 | 0.08798 | 0.06347 |
| $T_3$ | 0.09118 | 0.0955 | 0.10109 | 0.07337 |
| $\alpha_S$ | 0.82929 | 0.82662 | 0.82136 | 0.81998 |
| $\beta_S$ | 0.72452 | 0.71624 | 0.71484 | 0.7093 |
| X | 0.636 | 0.646 | 0.662 | 0.634 |
| Y | 0.610 | 0.625 | 0.633 | 0.586 |
| Z = \|X − Y\| | 0.026 | 0.021 | 0.029 | 0.048 |

TABLE 5

| Measurement | LIGHT SOURCE | | | |
| --- | --- | --- | --- | --- |
| | 650 nm | 660 nm | 685 nm | 810 nm |
| $T_1$ | 0.04775 | 0.05095 | 0.05462 | 0.03209 |
| $T_2$ | 0.05782 | 0.06186 | 0.06706 | 0.03954 |
| $T_3$ | 0.06901 | 0.0735 | 0.08006 | 0.04748 |
| $\alpha_S$ | 0.82587 | 0.82359 | 0.81444 | 0.81156 |
| $\beta_S$ | 0.69193 | 0.69319 | 0.68215 | 0.67573 |
| X | 0.649 | 0.657 | 0.687 | 0.664 |
| Y | 0.682 | 0.676 | 0.705 | 0.654 |
| Z = \|X − Y\| | 0.033 | 0.019 | 0.018 | 0.010 |

The values of X and Y for these two samples are much closer than the values listed in Table 3 for the 0.10 Hct sample. In the data listed in Table 5 for the 0.30 Hct sample, the value of Z at each wavelength is no more than about 5% of the X and Y values, with the Z measurements at most wavelengths being less than 3% of those values. It seems safe to conclude that these samples are incoherently scattering because X and Y do not differ by very much. In correcting these transmission measurements, one could simply assume that the scattering is a fixed number and can factor out this fixed offset as outlined above.

In the data listed in Table 4 for the 0.20 Hct sample, this is not as clear—the values of Z range from a little over 3% to about 8%. One could assume this sample is incoherently scattering at least those wavelengths with the lower Z values and correct the measurements by factoring out the fixed scattering offset. However, it may not be as accurate to make this assumption for the wavelengths with the higher values of Z. Accordingly, it would be advisable for those wavelengths to assume that the sample may be coherently scattering and to use a lower value for the scattering offset. The precise scattering offset can be determined, for example, by looking up the value in a look-up table or by calculating the value relying on the generally linear relationship with the hematocrit, as mentioned above.

While a preferred embodiment of the present invention has been described, it should be understood that various changes, adaptations and modifications may be made therein without departing from the spirit of the invention and the scope of the appended claims.

What is claimed is:

1. A method of measuring radiation absorption of a sample, comprising:
   a) providing an analyzer including a radiation source, a sample holder, a radiation detector, and a selectively operable radiation occluder positioned between the source and the detector along a radiation path;
   b) placing a sample in the sample holder;
   c) positioning the occluder at a first position; directing radiation from the source toward the sample; and taking a first radiation measurement with the detector;
   d) positioning the occluder at a second position, the percentage of radiation occluded by the occluder in the second position being different from the percentage of radiation occluded in the first position; directing radiation from the source toward the sample; and taking a second radiation measurement with the detector;
   e) positioning the occluder at a third position, the percentage of radiation occluded by the occluder in the third position being different from the percentage of radiation occluded in either of the first or second positions; directing radiation from the source toward the sample; and taking a third radiation measurement with the detector;
   f) comparing the first, second and third radiation measurements to determine radiation attenuation attributable to scattering by the sample; and
   g) factoring out said radiation attenuation attributable to scattering to determine a radiation absorption value for the sample.

2. The method of claim 1 wherein the comparison of the first, second and third measurements comprises calculating a first ratio as a ratio of the second measurement to the first measurement; calculating a second ratio as a ratio of the third measurement to the first measurement; and comparing the first and second ratios to determine whether the sample scatters the radiation and, if so, whether the scattering is coherent or incoherent.

3. The method of claim 2 wherein said attenuation attributable to scattering is factored out if scattering is determined to be coherent by dividing out a fixed scattering coefficient.

4. The method of claim 2 wherein said attenuation attributable to scattering is factored out if scattering is determined to be incoherent by
   a) subtracting the second ratio from the first ratio;
   b) determining a variable scattering coefficient which is directly proportional to the difference between the first and second ratios; and
   c) dividing out the variable scattering coefficient.

5. The method of claim 1 wherein the radiation source radiates visible light and the radiation detector is a photometer, the steps of taking said first, second and third radiation measurements comprising measuring photons at said photometer.

6. The method of claim 1 wherein the occluder is positioned to occlude more radiation in its third position than in either its first position or its second position.

7. The method of claim 6 wherein the first radiation measurement is taken prior to taking the second radiation measurement.

8. The method of claim 7 wherein the second radiation measurement is taken prior to taking the third radiation measurement.

9. The method of claim 1 wherein the occluder is positioned along the radiation path between the radiation source and the sample container in each of its first, second and third positions.

10. The method of claim 1 wherein the occluder comprises a moveable plate having an area which is highly transmissive of radiation in a predetermined band of wavelengths and at least one area which is less transmissive of radiation in said band of wavelengths, the occluder being moved between its first, second and third position by varying the position of the plate with respect to the radiation path.

11. The method of claim 10 wherein the plate comprises a sheet having a first transmission-reducing dot and a second transmission-reducing dot, the second dot having a larger surface area than the first dot, the occluder being positioned in its first position by positioning the sheet without any dot along the radiation path, in its second position by positioning the first dot along the radiation path, and in its third position by positioning the second dot along the radiation path.

12. The method of claim 10 wherein the plate comprises a sheet having a transmission-reducing dot, the occluder being positioned in its first position by positioning the sheet without any dot along the radiation path, in its second position by positioning a portion of the dot along the radiation path, and in its third position by positioning a different portion of the dot along the radiation path.

13. The method of claim 12 wherein the entire dot is positioned along the radiation path when the occluder is positioned in its third position, and less than the entire dot is positioned along the radiation path when the occluder is positioned in its second position.

14. A method of measuring light absorption of a light-scattering sample, comprising:
   a) providing an analyzer including a light source, a sample holder, a light detector, and a selectively operable occluder positioned between the source and the detector along a light path;
   b) placing a sample in the sample holder;
   c) positioning the occluder at a first position; directing light from the source toward the sample; and taking a first light measurement with the detector;
   d) positioning the occluder at a second position, the percentage of light occluded by the occluder in the second position being different from the percentage of light occluded in the first position; directing light from the source toward the sample; and taking a second light measurement with the detector;
   e) positioning the occluder at a third position, the percentage of light occluded by the occluder in the third position being different from the percentage of light occluded in either of the first or second positions; directing light from the source toward the sample; and taking a third light measurement with the detector;
   f) comparing the first, second and third light measurements to determine light attenuation attributable to scattering caused by the sample; and
   g) factoring out said attenuation attributable to scattering to determine a light absorption value for the sample.

15. The method of claim 14 wherein the comparison of the first, second and third measurements comprises calculating a first ratio as a ratio of the second measurement to the first measurement; calculating a second ratio as a ratio of the third measurement to the first measurement; and comparing the first and second ratios to determine whether the sample scatters the radiation and, if so, whether the scattering is coherent or incoherent.

16. The method of claim 15 wherein said attenuation attributable to scattering is factored out if scattering is determined to be coherent by dividing out a fixed scattering coefficient.

17. The method of claim 15 wherein said attenuation attributable to scattering is factored out if scattering is determined to be incoherent by
   a) subtracting the second ratio from the first ratio;
   b) determining a variable scattering coefficient which is directly proportional to the difference between the first and second ratios; and
   c) dividing out the variable scattering coefficient.

18. The method of claim 14 wherein the occluder is positioned to occlude more light in its third position than in either its first position or its second position.

19. The method of claim 18 wherein the first light measurement is taken prior to taking the second light measurement.

20. The method of claim 19 wherein the second light measurement is take prior to taking the third light measurement.

21. The method of claim 14 wherein the occluder is positioned between the source and the sample container in each of its first, second and third positions.

22. The method of claim 14 wherein the occluder comprises a moveable plate having an area which is highly transmissive of light in a predetermined band of wavelengths and at least one area which is less transmissive of light in said band of wavelengths, the occluder being moved between its first, second and third position by varying the position of the plate with respect to the light source.

23. The method of claim 22 wherein the plate comprises a transparent sheet having a first transmission-reducing dot and a second transmission-reducing dot, the second dot being larger than the first dot, the occluder being positioned in its first position by positioning the transparent sheet between the source and the detector, in its second position by positioning the first dot between the source and the detector, and in its third position by positioning the second dot between the source and the detector.

24. The method of claim 22 wherein the plate comprises a sheet having a transmission-reducing dot, the occluder being positioned in its first position by positioning the sheet without any dot along the radiation path, in its second position by positioning a portion of the dot along the radiation path, and in its third position by positioning a different portion of the dot along the radiation path.

25. The method of claim 24 wherein the entire dot is positioned along the radiation path when the occluder is positioned in its third position, and less than the entire dot is positioned along the radiation path when the occluder is positioned in its second position.

26. The method of claim 25 wherein the sample comprises a blood sample, further comprising the step of determining hemoglobin concentration for the sample based on said light absorption value.

27. The method of claim 14 wherein the occluder comprises a first and second polarizing plates, the first polarizing plate being positioned between the light source and the sample holder and the second polarizing plate being positioned between the sample holder and the light detector, the occluder being moved between its first, second and third positions by varying the relative orientation of the first and second polarizing plates along the optical path.

28. The method of claim 27 wherein at least one of the first and second polarizing plates is rotatable about a rotational axis generally orthogonal to each of the first and second polarizing pates, the occluder being moved from its first position to its second position by rotating said at least one polarizing plate about the rotational axis to a position wherein the phase relationship of the first and second polarizing plates differs from the phase relationship of the first and second polarizing plates in the first position.

29. An analyzer for measuring light attenuation of a sample comprising:
   a) a light source;
   b) a sample holder;
   c) a light detector;
   d) a selectively controllable light occluder positioned between the light source and the light detector along a light path, the occluder comprising a plate having an area which is highly transmissive of light at a predetermined wavelength and at least one area which is less transmissive of light at said wavelength; and
   e) a motor for moving the occluder between a first position wherein the plate of the occluder is positioned relative to the light path to occlude a first percentage of the light, a second position wherein the plate of the occluder is positioned relative to the light path to occlude a second percentage of the light, and a third position wherein the plate of the occluder is positioned relative to the light path to occlude a third percentage of the light.

30. The analyzer of claim 29 wherein the plate comprises a transparent sheet having a first transmission-reducing dot and a second transmission-reducing dot, the second dot being larger than the first dot, a location of the transparent sheet without a transmission-reducing dot being disposed along the light path when the occluder is in its first position, the first dot being disposed along the light path when the occluder is in its second position, and the second dot being disposed along the light path when the occluder is in its third position.

31. An analyzer for measuring light attenuation of a sample comprising:
   a) a light source;
   b) a sample holder;
   c) a light detector;
   d) an occluder comprising first and second polarizing plates, the first polarizing plate being positioned between the light source and the sample holder along a light path and the second polarizing plate being positioned between the sample holder and the light detector along the light path; and
   e) at least one motor for moving the at least one of the first and second polarizing plates with respect to the other from a first relative orientation wherein the polarizing plates of the occluder occlude a first percentage of the light, a second relative orientation wherein the polarizing plates occlude a second percentage of the light, and a third relative orientation wherein the polarizing plates occlude a third percentage of the light.

\* \* \* \* \*